United States Patent
Riley

(10) Patent No.: US 6,533,116 B1
(45) Date of Patent: Mar. 18, 2003

(54) MEDICAL INSTRUMENT CONTAINER

(75) Inventor: Kimberly M. Riley, Boylston, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/638,624

(22) Filed: Aug. 15, 2000

(51) Int. Cl.[7] .............................. B65D 85/04; B65B 7/00
(52) U.S. Cl. ...................... 206/363; 53/467; 206/493
(58) Field of Search ................ 206/363, 364, 206/365, 366, 367, 368, 369, 370, 372, 373, 438, 470, 471, 493, 570, 571, 572, 388, 461, 464, 467; 53/467

(56) References Cited

U.S. PATENT DOCUMENTS

| | | | |
|---|---|---|---|
| 2,699,865 A | * | 1/1955 | Bowden .................... 206/373 |
| 4,168,779 A | | 9/1979 | Yokokoji et al. |
| 4,170,300 A | * | 10/1979 | Pick ............................ 206/365 |
| 4,206,844 A | | 6/1980 | Thukamoto et al. |
| 4,262,800 A | * | 4/1981 | Nethercutt ................... 206/364 |
| 4,901,884 A | | 2/1990 | Kallenbach |
| 4,928,830 A | * | 5/1990 | Brewer ....................... 206/570 |
| D310,563 S | | 9/1990 | Greengrass et al. |
| 4,986,438 A | | 1/1991 | Borst |
| 5,031,768 A | * | 7/1991 | Fischer ....................... 206/370 |
| 5,031,775 A | * | 7/1991 | Kane .......................... 206/571 |
| 5,311,990 A | * | 5/1994 | Kalinski ..................... 206/370 |
| 5,348,031 A | | 9/1994 | Cloud |
| D354,910 S | | 1/1995 | Weatherford et al. |
| 5,407,071 A | * | 4/1995 | Lawhon et al. ............. 206/388 |
| D358,763 S | | 5/1995 | Weatherford et al. |
| 5,493,848 A | | 2/1996 | McKibben et al. |
| 5,522,255 A | | 6/1996 | Neel et al. |
| 5,566,828 A | * | 10/1996 | Claes et al. ................. 206/570 |
| 5,755,323 A | | 5/1998 | Zahn et al. |
| 5,775,516 A | | 7/1998 | McCumber et al. |
| 5,942,438 A | | 8/1999 | Antonplos et al. |
| 5,954,203 A | * | 9/1999 | Marconi ..................... 206/464 |
| 6,012,580 A | * | 1/2000 | Peters et al. ................ 206/438 |
| 6,076,665 A | * | 7/2000 | Chaung ...................... 206/493 |
| 2001/0027618 A1 | | 10/2001 | Fallon et al. |

* cited by examiner

*Primary Examiner*—Jim Foster
(74) *Attorney, Agent, or Firm*—Finnegan, Henderson, Farabow, Garrett & Dunner, LLP

(57) ABSTRACT

A medical container for holding a medical instrument. The container includes a cover, a base, and a flexible hinge. Portions of the base and cover form a holding portion and a locking portion. The holding portion includes two different holding cavities to hold different shaped medical instruments. The container arrangement allows the medical instrument to be removed during an operation or procedure, and returned to the container after it has been used. This protects the medical instrument from the environment while it is staged during the operation.

17 Claims, 7 Drawing Sheets

MEDICAL INSTRUMENT CONTAINER

DESCRIPTION OF THE INVENTION

1. Field of the Invention

The present invention relates to medical instrument containers in general, and reusable medical containers capable of holding different instruments in particular.

2. Background of the Invention

Medical containers or trays are used to provide storage and protection for medical instruments. A typical medical container includes three separate pieces. Two separate pieces are designed to hold the instrument in a preferred orientation, and the third piece is applied to seal the instrument inside the container. By sealing the instrument between the two separate pieces, the tray provides a sterile environment to protect the instrument from germs and other pollutants. These medical containers are usually formed from polyethylene terephthalate, glycol modified (PETG) or other thermoplastic materials.

Often these containers are formed from large sheets of thermoplastic material and provide excess material to protect the instruments from harm. Because of their size, these medical containers are both expensive to manufacture and cumbersome to carry in the operating room. In addition, each medical container is designed to fit the shape of a particular medical instrument, resulting in a multitude of different containers. Even similar medical instruments may require different container designs, depending upon variations that exist between the instruments. For example, a sphincterotome can have different shaped mandrils, requiring a different shaped container for each mandril shape.

A medical instrument remains stored in its container until it is needed during a procedure. In a typical procedure, several different medical instruments may be required. Therefore, depending on the complexity of the procedure, it is common to find several containers in an operating room. When a medical instrument is needed, the container is opened and the instrument is removed. The container is then thrown away because it is not designed for reuse. After the medical instrument is used, it may be draped across tables or other surfaces for ready access. This process is known as staging the medical instrument. Several instruments may be opened and exposed to the environment in this manner. This is undesirable because the instruments may be damaged and take up needed space in the operating room. It is common practice to place a pillow cover over the end of the instrument to provide some protection for the medical instrument, but this does not solve the problem of taking up needed space and typically does not provide sufficient protection to the instrument.

SUMMARY OF THE INVENTION

Accordingly, the present invention is directed to a medical container capable of holding different shaped medical instruments in a compact form. In addition, the present invention is directed to a medical container that can be opened and reused throughout a medical procedure.

To achieve these and other advantages and in accordance with the purpose of the invention, as embodied and broadly described herein, the invention is directed to a container for holding medical instruments. The container includes a base, a cover, a locking portion configured to secure the cover to the base in a closed position, and a holding portion. The locking portion includes a first portion in the cover and a second portion in the base. The first and second portions have corresponding shapes to mate with one another and secure the cover in the closed position. The holding portion has a first and a second section for selectively holding a first medical instrument of a first shape and a second medical instrument of a second shape respectively in a secured position. In another aspect, each of the first and second sections includes a recessed portion on the cover, and a holding cavity in the base. The recessed portion cooperates with the holding cavity to secure one of the first medical instrument and the second medical instrument therein. In yet another aspect, the container includes a hinge connecting the cover to the base. In a further aspect, the base, the hinge, and the cover are formed as a unitary piece. In another aspect, the base includes a hole for hanging the container. In yet another aspect, each of the first and second sections includes a cavity capable of securing a first free end of one of the first medical instrument and the second medical instrument. In a further aspect, the base includes an instrument post adapted to retain a second free end of one of the first medical instrument and the second medical instrument. In another aspect, the first portion is one of an extended securing portion and a receiving portion, the second portion being the other of the extended securing portion and the receiving portion. The securing portion mates with the receiving portion when the cover is in the closed position. In yet another aspect, the cover includes a first cover recessed portion configured to cover the first section when the cover is in the closed position, and a second cover recessed portion configured to cover the second section when the cover is in the closed position. In still another aspect, the container includes one of the first medical instrument and the second medical instrument having a free end secured in the respective section when the cover is in the closed position. In a further aspect, the base includes an instrument post. The medical instrument includes a handle, and the instrument post is capable of securing the handle to the base.

In another aspect, the present invention is directed to a method of packaging a medical instrument in a medical container. The medical instrument includes a handle and an end distal from the handle. The medical container includes a cover, a base, a locking portion, and a holding portion. The locking portion has a securing portion on one of the cover and the base and a receiving portion on other of the cover and the base. The securing portion is capable of cooperating with the receiving portion to secure the cover in a closed position. The holding portion has first and second sections for selectively holding the medical instrument in a secured position in one of the first section and the second section. The method includes placing the end of the medical instrument in one of the first section and the second section depending on the shape of the medical instrument, and closing the cover of the medical container onto the base of the medical container. Closing the cover causes the locking portion to secure the cover in the closed position and secure the medical instrument in one of the first and second sections. In another aspect, the medical container includes an instrument post, and the method includes securing the handle of the medical instrument to the instrument post. In a further aspect, the step of securing the handle of the medical instrument to the instrument post includes pressing the handle onto the instrument post. In another aspect, each of the first and second sections includes a recessed portion on the cover and a holding cavity in the base. The recessed portion is capable of cooperating with the holding cavity to secure the medical instrument therein. The step of placing the end of the medical instrument in one of the first and second sections further includes placing the end of the medical instrument in the holding cavity.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings.

DESCRIPTION OF THE PREFERRED EMBODIMENTS

Reference will now be made in detail to the present preferred embodiments of the invention, examples of which are illustrated in the accompanying drawings. Wherever possible, the same reference numbers will be used throughout the drawings to refer to the same or like parts.

The medical container of the present invention includes a cover and a base. The cover can be attached to the base with, for example, a flexible hinge. The cover and the base include cooperating structural elements that secure the cover to the base in a closed position and also retain a medical instrument in a secured fashion. For example, the cover includes a recessed portion and several securing portions, and the base includes several securing valleys, securing hollow portions, and channels. The securing portions on the cover cooperate with the securing valleys and hollow portions on the base to secure the cover to the base. The recessed portion on the cover cooperates with the channels on the base to secure a medical instrument in the container.

The medical instrument container of the present invention is preferably formed from a single sheet of material, reducing the number of pieces necessary to manufacture the medical container. In addition, the medical instrument container is designed to retain a variety of similar shaped medical instruments, reducing the number of different containers necessary to hold the instruments. As a result, the medical container is less expensive, easier to manufacture, and more versatile than conventional containers.

During a medical procedure, the instrument is removed from the container and then returned to the container to be reused later if necessary. By returning the medical instrument to the medical container, the instrument can be protected from contaminants or possible damage while it is not being used. In addition, the medical instrument will take up less space than if it were draped over an available surface in the operating room.

The embodiments of the medical container according to the present invention that are shown in the Figures and described below include structure and parts of particularly described shapes and sizes. The inventive medical container and its associated structure, however, is not limited to the particular shapes or sizes shown and described. One skilled in the art would understand that other shaped and sized parts of the medical container may be suitable depending on, for example, the type of medical instrument held by the container.

Figure 1:
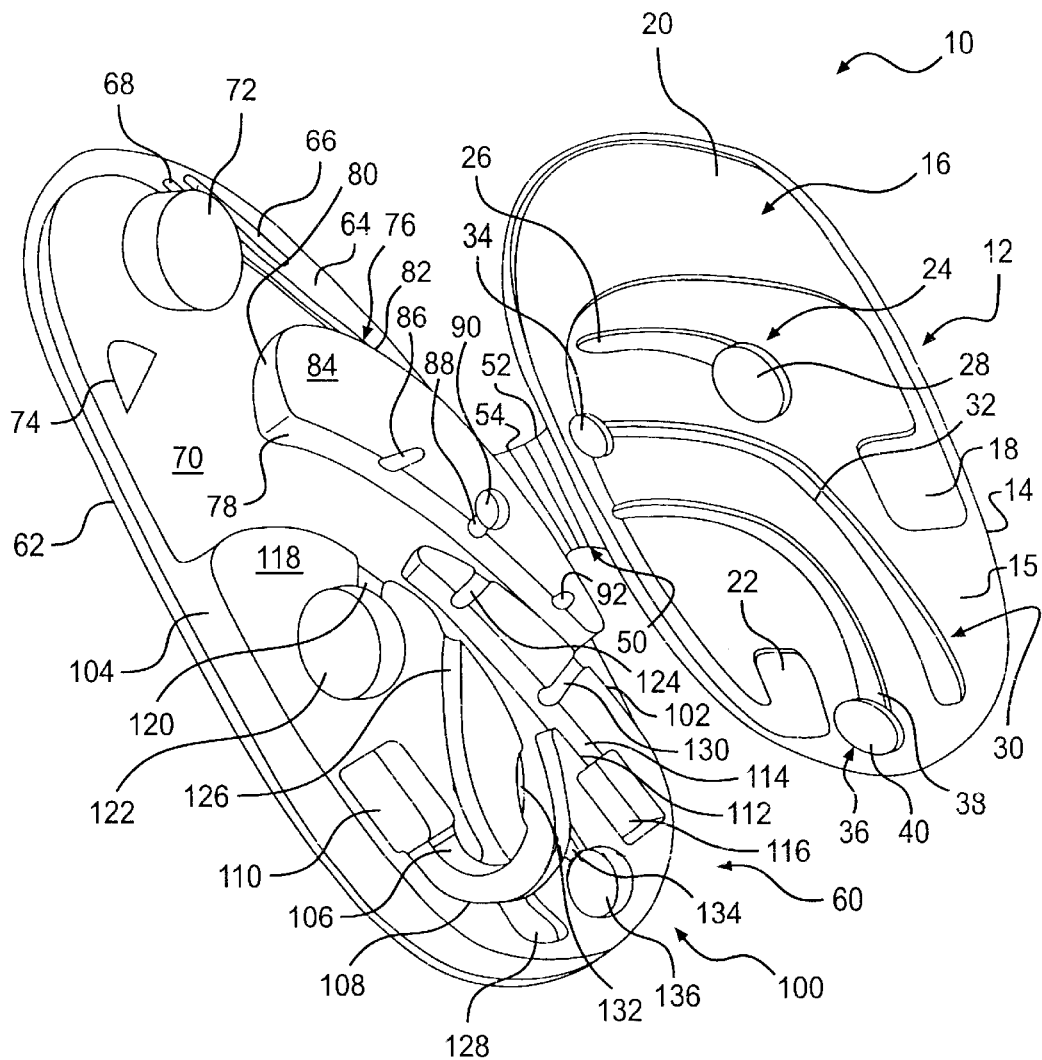
FIG. 1 is perspective view of a first embodiment of a medical container of the invention in the open position.
Figure 2:
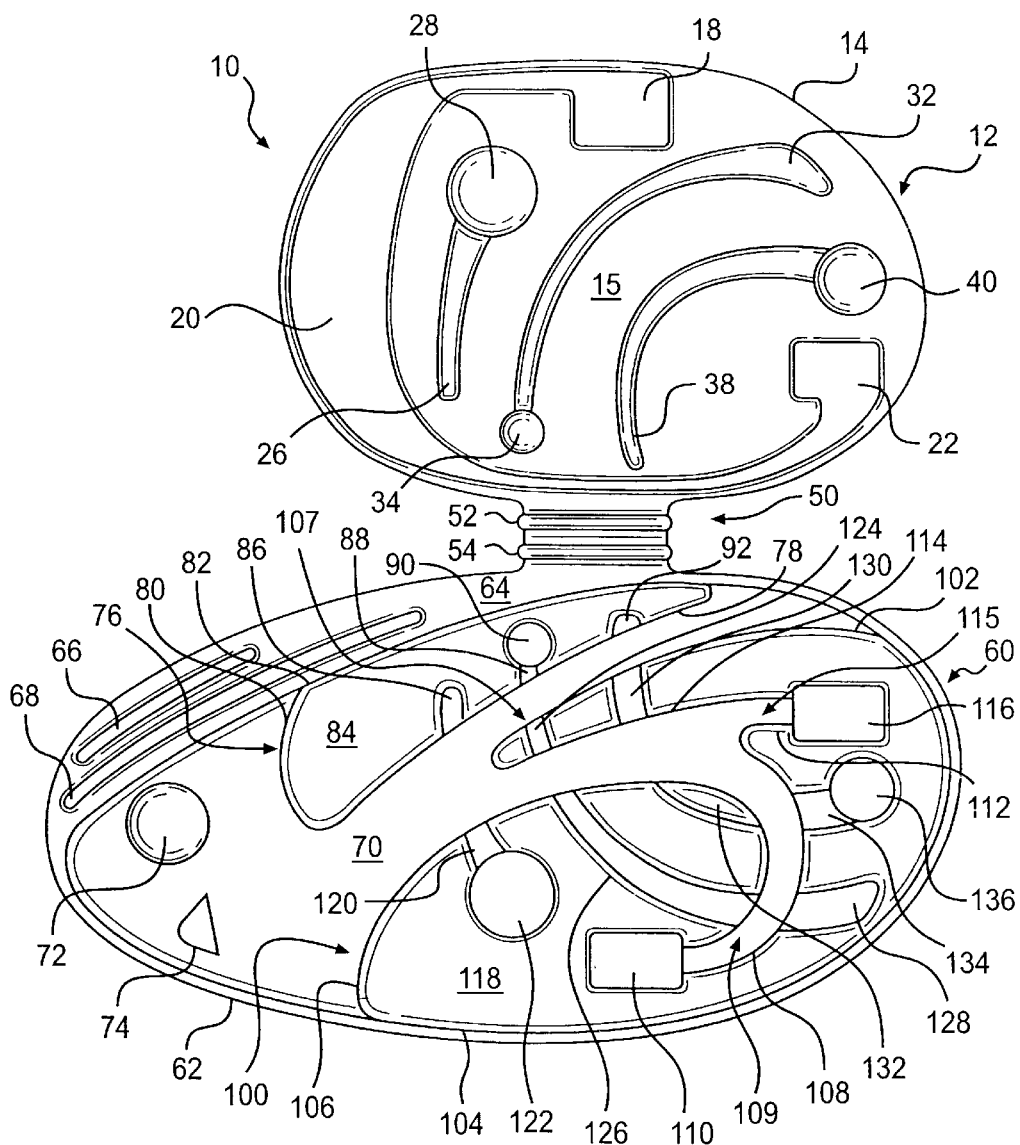
FIG. 2 is a plan view of the medical container of FIG. 1.

A first embodiment of a medical container according the present invention is shown in FIGS. 1 and 2, as container 10. The container is formed preferably from a thermoplastic sheet, and more preferably from PETG. Other suitable, like materials may be used with the medical container of the present invention and the invention is not limited to a particular material. The container 10 includes a cover 12, a hinge 50, a base 60, a locking portion, and a holding portion. The locking portion and holding portion will be described in detail below.

The cover 12 has an inner surface 15 and a perimeter 14 with, in a preferred embodiment, a generally oval shape. Cover 12 and therefore perimeter 14, may have other shapes, as desired. The inner surface 15 includes a recessed portion 16 which has a depth of preferably approximately two millimeters. The recessed portion 16 includes a first end 18, a connecting section 20, and a second end 22. The first end 18 and second end 22 help retain a medical instrument (not shown in FIGS. 1 and 2) in the container 10. The inner surface 15 also includes three securing portions 24, 30, and 36. Each securing portion 24, 30, and 36 includes a securing rib portion 26, 32, 38, and a securing stub 28, 34, 40, respectively. Each securing rib portion 26, 32, and 38 extend upwards from the inner surface preferably approximately two millimeters. The securing stubs 28, 34, and 40 are substantially circular, although other shapes such as square, rectangular, or any other desired shape can work equally well. Each stub extends upward from the inner surface preferably approximately five millimeters, and the diameters of the stubs can vary from, for example, approximately one to two centimeters, although other diameters will work equally well.

The base 60 has an inner surface 64 and in this embodiment, a substantially oval perimeter 62. The inner surface 64 includes reinforcement ribs 66 and 68, each of which depend from the inner surface 64 preferably approximately one millimeter. A base raised surface 70 extends upward from the inner surface 64 preferably approximately four millimeters. The base raised surface 70 includes an instrument post 72, for holding the handle of the medical instrument, and a hole 74 for hanging the container 10. In a preferred arrangement, the instrument post 72 is substantially circular with a diameter of approximately twenty-three millimeters, and a height of approximately seven millimeters. The instrument post 72 is shown as substantially circular, however, any shape that can hold an instrument handle is acceptable. By providing an instrument post, a portion of the handle of the medical instrument can be secured to the container. During a medical procedure, the container 10 can be hung from a hook using another portion of the handle of the medical instrument or the hole 74.

In addition, extending from the base raised surface 70 is a first raised platform 76, and a second raised platform 100. Both raised platforms extend preferably approximately six millimeters upward from the base raised surface 70. The first raised platform includes an inner wall 78, end wall 80, and outer wall 82, and a top surface 84. The top surface 84 includes securing valley portions 86, 88, 92, and a securing hollow portion 90. The second platform 100 includes an inner wall 102, an outer wall 104, a first channel wall 106, a second channel wall 108, a first holding cavity 110, a third channel wall 112, a fourth channel wall 114, a second holding cavity 116, and a top surface 118. The first holding cavity 110 and second holding cavity 116 extend below the raised surface 70 preferably approximately nine millimeters, and have a length of preferably approximately twenty millimeters and a width of preferably approximately fourteen millimeters. The top surface 118 includes securing valley portions 120, 124, 126, 128, 134, a securing cut-out 132, and securing hollow portions 122 and 136. Each of the securing valley portions on the first raised platform 76 and second raised platform 100 depend from-the top surface preferably approximately three millimeters. Each of the securing hollow portions on the first and second raised platform depends from the top surface preferably approximately five millimeters. The locking portion of the container will be described in detail below.

The hinge 50 extends from the perimeter 14 of the cover 12 to the perimeter 62 of the base 60. The hinge 50 includes two bent portions 52, and 54, that extend parallel to the perimeter 14 of the cover 12. These bent portions 52, 54 allow the hinge 50 to flex when the cover 12 is closed.

A routing channel 107, best shown in FIG. 2, for holding excess lengths of the medical instrument is defined by inner wall 78, inner wall 102, and raised surface 70. A first instrument channel 109 is defined by first channel wall 106, second channel wall 108, and raised surface 70. The first instrument channel 109 ends in first holding cavity 110 and is intended to hold a medical instrument with a curved end. A second instrument channel 115 is defined by third channel wall 112 and fourth channel wall 114. The second instrument channel 115 ends in a second holding cavity 116 and is intended to hold a medical instrument with a straight end. To secure the medical instrument in either the first holding cavity 110 or the second holding cavity 116, the cover is closed. In the closed position, the first end 18 of the recessed portion 16 in the cover 12 overlays the first holding cavity 110, and the second end 22 of the recessed portion 16 overlays the second holding cavity 116.

Figure 3:
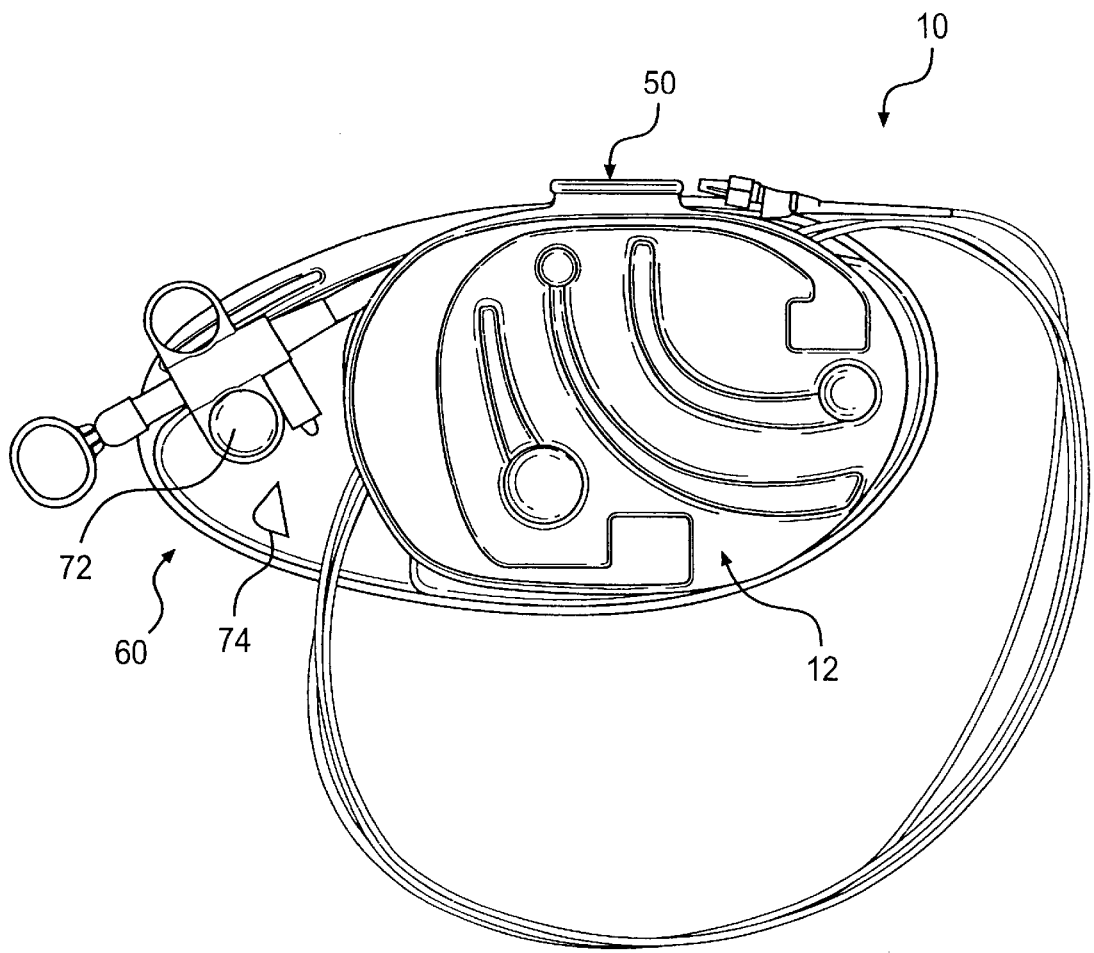
FIG. 3 is a plan view of the medical container of FIG. 1 in a closed position and holding a medical instrument.

To secure the cover 12 to the base 60, as seen in FIG. 3, the securing portions 24, 30, and 36 must cooperate with the base 60. With regards to securing portion 24, the securing rib portion 26 cooperates with securing valley 86 and securing valley 120; and the securing stub 28 cooperates with securing hollow portion 120. With regards to securing portion 30, the securing rib portion 32 cooperates with securing valleys 88, 124, 126, and 128; and the securing stub 34 cooperates with securing hollow portion 90. With regards to securing portion 36, the securing rib portion 38 cooperates with securing valley 92, securing cut-out 130, and securing valley 132; and the securing stub 40 cooperates with securing hollow portion 134. When the cover 12 is closed, the securing portions 24, 30, and 36 fit within the securing valleys and hollow portions, frictionally retaining the cover 12 in the closed position. Several other shapes exist for the securing portions and securing hollow portions, and are within the scope of this invention, which would allow the cover to be secured to the base.

Figure 4:
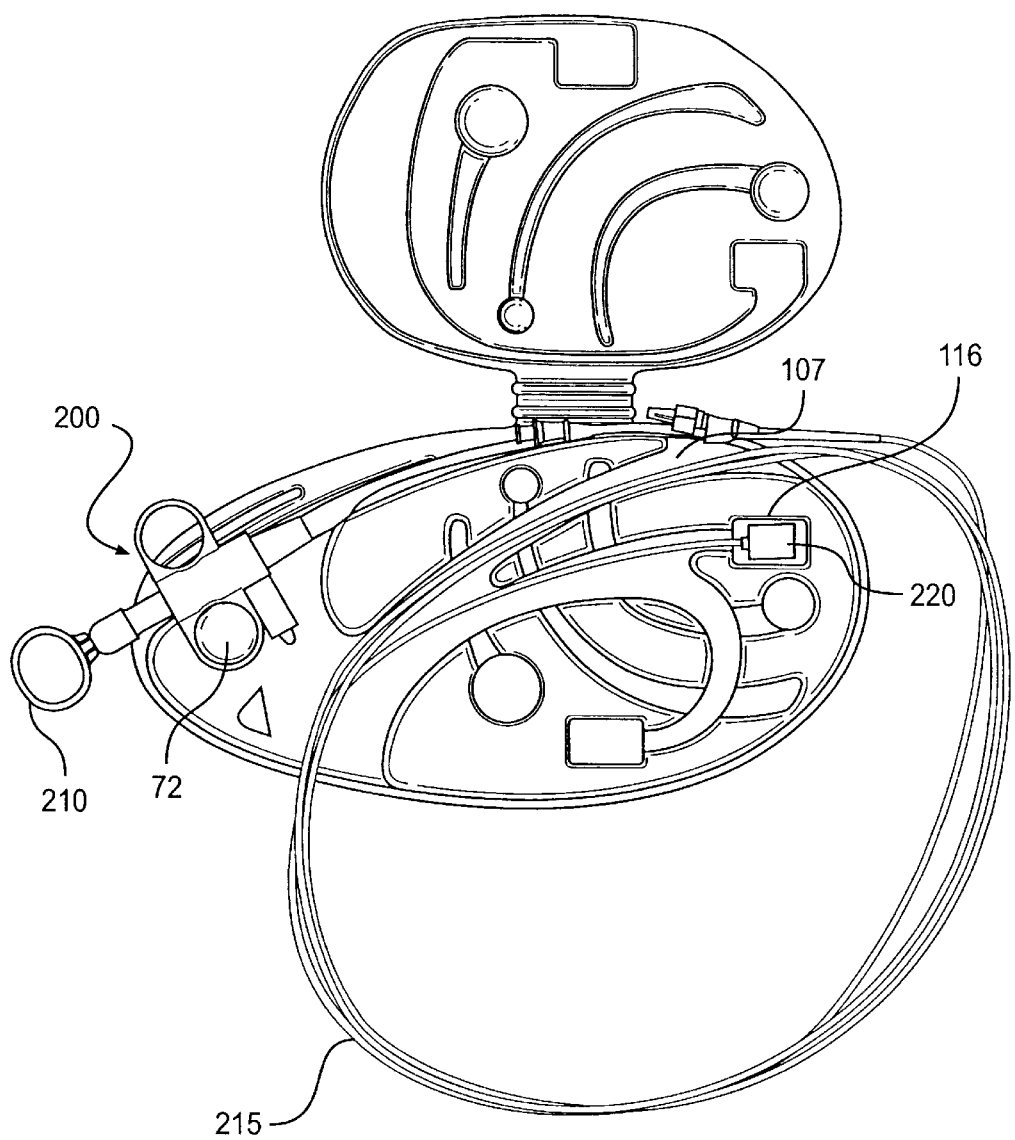
FIG. 4 is a plan view of the medical container of FIG. 2 in an open position holding a medical instrument in a first position.

As seen in FIG. 4, the container 10 can hold a medical instrument 200. The medical instrument may be, for example, a sphincterotome having a straight mandril 220, flexible tube 215, and a handle 210. The handle 210 is pressed onto the instrument post 72 of the base 60. The flexible tube 215 is wrapped a few times through the routing channel 107. The mandril 220 is inserted into the second holding cavity 116. When the cover 12 is closed and locked in place, the sphincterotome is substantially fixedly secured in the container 10, as seen in FIG. 3.

Figure 5:
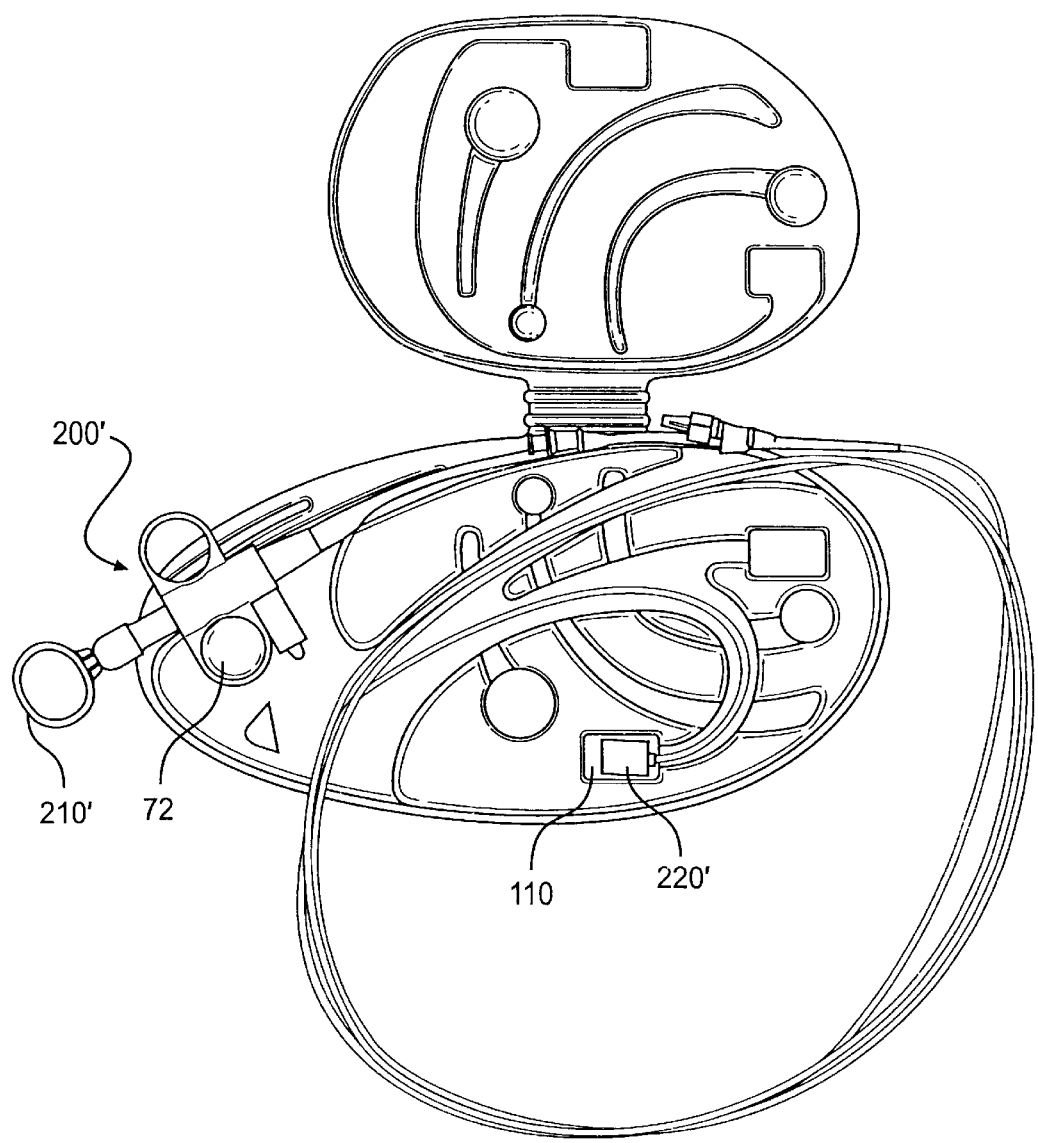
FIG. 5 is a plan view of the medical container of FIG. 2 in an open position holding a medical instrument in a second position.

FIG. 5 shows a medical instrument 200' with a curved mandril 220' and handle 210'. In this arrangement, the curved mandril 220' is held in the first holding cavity 110, to maintain the shape of the curved mandril 220'. When the cover 12 is closed and locked in place, the sphincterotome is substantially fixedly secured in the container 10, as seen in FIG. 4.

Figure 6:
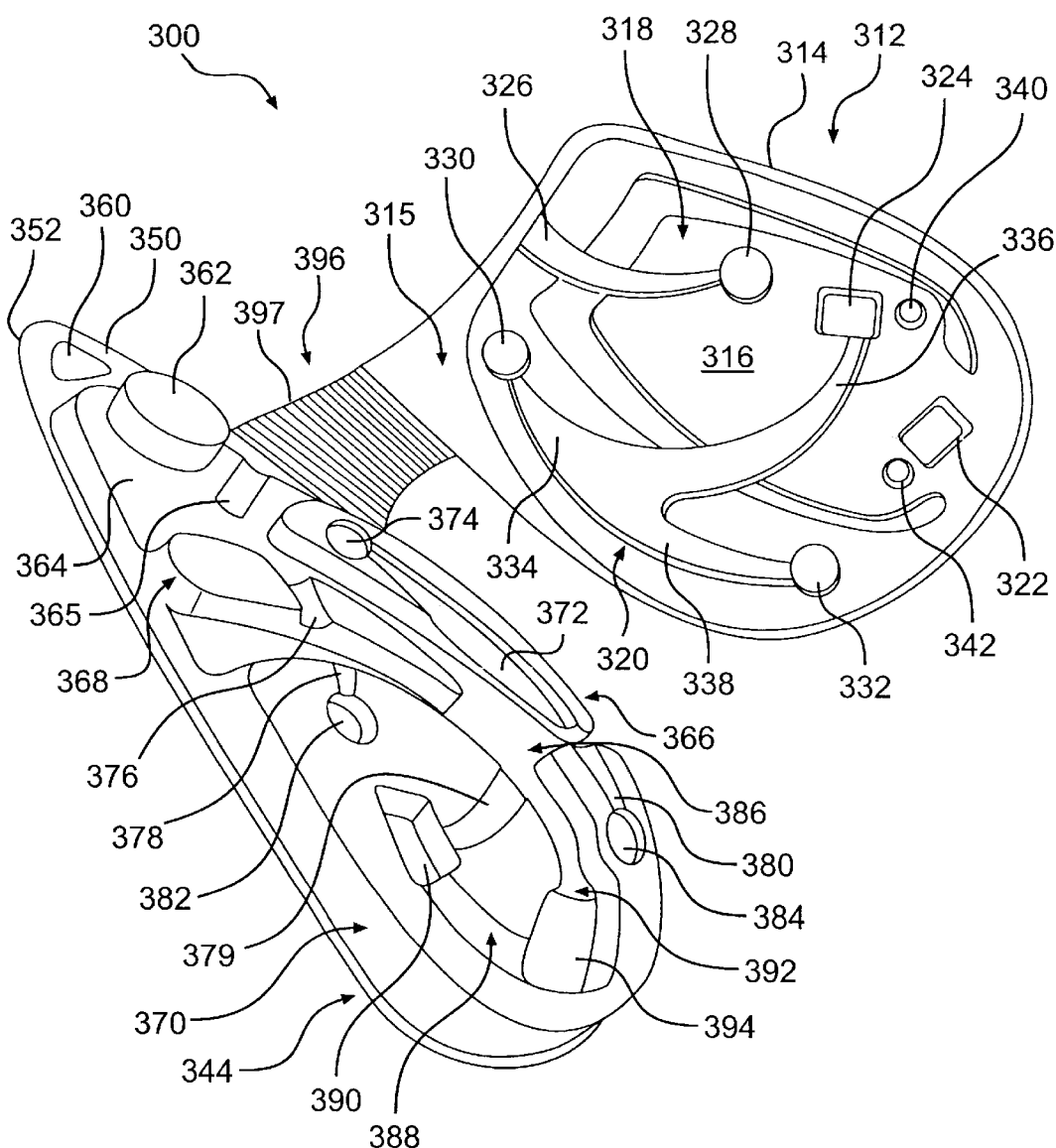
FIG. 6 is a perspective view of a second embodiment of a medical container of the invention in an open position.
Figure 7:
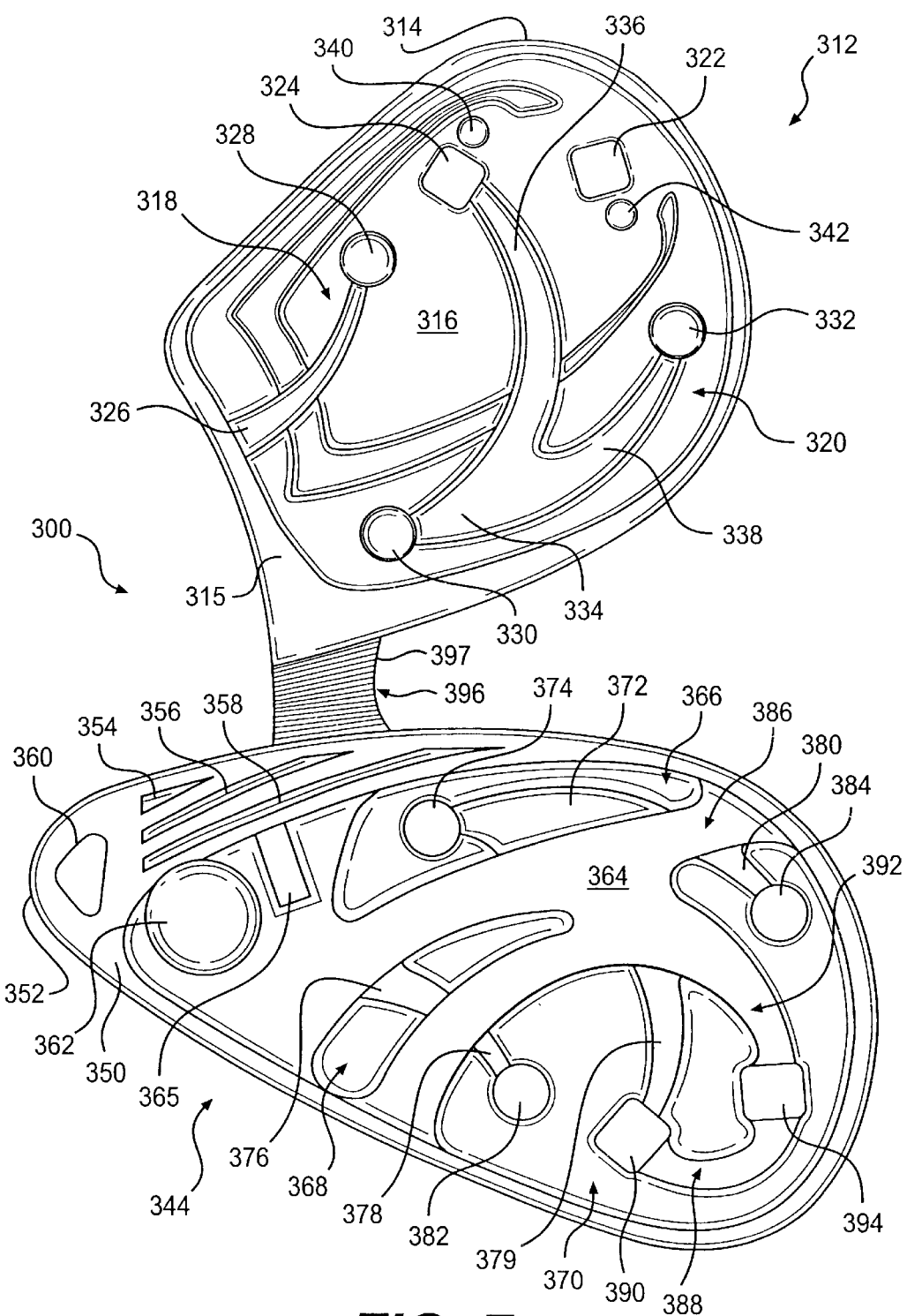
FIG. 7 is a plan view of the medical container of FIG. 6.

A second embodiment of a medical container according to the present invention is shown in FIGS. 6 and 7, as container 300. A cover 312 of container 300 has an inner surface 315, an outer surface, and a perimeter 314 with a generally oval shape. The inner surface 315 has a raised surface 316 similar to the raised surface of the medical container of the first embodiment. The raised surface 316 includes two securing portions 318, 320, and two recessed portions 322, 324. The two recessed portions 322, 324 serve a similar purpose as the first and second ends of the recessed portion in the medical container of the first embodiment. Securing portion 318 includes a securing rib portion 326 and a securing stub 328. The other securing portion 320 includes two securing stubs 330, 332 and one of the recessed portions 324. A securing rib 334 extends from securing stub 330 and branches into securing ribs 336, 338 ending in the recessed portion 324 and securing stub 332, respectively. The securing portions functions as part of the locking portion as described above in the medical container of the first embodiment. Located next to each of the recessed portions 322, 324 are raised buttons 340, 342. The purpose of the raised buttons 340, 342 will be described below in relation to the holding portion of the container.

The base 344 has an inner surface 346, an outer surface, an outer lip 350, and a perimeter 352 with a generally oval shape. Part of the outer lip 350 has three reinforcement ribs 354, 356, 358, which serve a similar function to the reinforcement ribs of the medical container of the first embodiment. The base 344 includes a hole 360 for hanging the container, and an instrument post 362 for securing a handle of a medical instrument to the container 10. During a medical procedure, the container 10 can be hung from a hook using another portion of the handle of the medical instrument or the hole 362 in the base 344. The base 344 includes a raised surface 364. The raised surface 364 includes preferably a shallow hollow 366 for orienting the handle of the medical instrument.

In addition, extending from the raised surface 364 of the base is a first raised platform 366, a second raised platform 368, and a third raised platform 370. The first platform 366 includes a securing valley portion 372 ending in a securing hollow portion 374. The second platform includes a securing valley portion 376. The third platform 370 includes securing valley portions 378, 380 ending in securing hollow portions 382, 384 respectively. An additional securing valley portion 379 is formed in the third platform 370. Each of the securing valley portions and securing hollow portions are similar to those of the medical container of the first embodiment. A routing channel 386, similar to the routing channel of the medical container of the first embodiment, is defined by surfaces of the platforms 366, 368, 370. A first instrument channel 388, similar to the first instrument channel of the medical container of the first embodiment, is defined by surfaces of the third platform 370. The first instrument channel 388 terminates in a first holding cavity 390. A second instrument channel 392, similar to the second instrument channel of the medical container of the first embodiment, is defined by surfaces of the second platform 368 and third platform 370. The second instrument channel 392 terminates in a second holding cavity 394.

A hinge 396 extends from the perimeter 314 of the cover portion 312 to the perimeter 355 of the base portion 344. The hinge 396 includes several notches 397 that extend substantially parallel to the perimeter 314 of the cover portion 312. These notches allow the hinge to flex.

The locking portion functions similarly to the locking portion of the medical container of the first embodiment. Specifically, when the cover is closed, the securing ridge 326 and securing post 328 cooperate with the securing valley portion 376 on the second platform, and the securing valley portion 378 and securing hollow portion 382 on the second platform 368. The securing stub 330 cooperates with securing hollow portion 374, and securing ridge 334 cooperates with securing valley portion 372. The securing stub 332 cooperates with securing hollow portion 384, and securing ridge 338 cooperates with securing valley portion 380. The securing ridge 336 cooperates with securing valley portion 379.

The holding portion of the second embodiment is similar to the holding portion of the medical container of the first embodiment. The first instrument channel 388 and first holding cavity 390 are configured to hold a medical instrument with a curved mandril. The second instrument channel 392 and second holding cavity 394 are configured to hold a medical instrument with a straight mandril. The raised buttons 340, 342, if included, provide additional assistance in keeping the mandril from sliding out of the holding cavities 390, 394 when the cover 312 is closed.

The medical container of the invention allows the medical instrument to be stored prior to the operation. During the operation, the instrument may be removed from the container and later placed back into the container until it is needed again later. This protects the instrument from being damaged, and provides a convenient form of storage. Instead of draping the medical instrument over a flat surface, the container, along with the medical instrument, can be hung from the hole in the base or the handle of the medical instrument. This arrangement will assist in freeing up the needed space in the operating room.

Other embodiments of the invention will be apparent to those skilled in the art from consideration of the specification and practice of the invention disclosed herein. For example, the container instrument channels can be arranged to hold different medical instruments other than the shown sphinctertome. In addition, the features of the locking portions can be reversed, where the securing portions are formed on the base and the securing valley portions and securing hollow portions are formed on the cover. It is intended that the specification and examples be considered as exemplary only, with a true scope and spirit of the invention being indicated by the following claims.

What is claimed is:

1. A container for holding a medical instrument, the container comprising:

a base having an edge at a perimeter, a first channel leading to an enlarged cavity, and a second channel leading to an enlarged cavity, wherein the second channel is nonaligned with the first channel, the first and second channel fork a common channel and the common channel extends away from the first and second channels to the edge;

a cover configured to close and secure a medical instrument in one of the first and second channels, the cover leaving the common channel laterally open at the edge when in a closed position; and a locking portion configured to secure the cover to the base in the closed position.

2. The container according to claim 1, further comprising a hinge connecting the cover to the base.

3. The container according to claim 2, wherein the cover, the hinge, and the base are formed as a unitary piece.

4. The container according to claim 1, wherein the base includes a hole for hanging the container.

5. The container according to claim 1, wherein the base includes an instrument post adapted to retain a free end of the medical instrument.

6. The container according to claim 1, wherein the locking portion includes a first portion in the cover and a second portion in the base and the first and second portions have corresponding shapes to mate with one another and secure the cover in the closed position.

7. The container according to claim 6, wherein the first portion includes a securing rib portion and the second portion includes a securing valley, and the securing rib portion mates with the securing valley when the cover is in the closed position.

8. The container according to claim 6, wherein the first portion includes a securing stub and the second portion includes a securing hollow portion, and the securing stub portion mates with the securing hollow portion when the cover is in the closed position.

9. The container according to claim 1, wherein the cover includes a first cover recessed portion configured to cover the first channel when the cover is in the closed position, and a second cover recessed portion configured to cover the second channel when the cover is in the closed position.

10. The container according to claim 1, further comprising the medical instrument in one of the first and second channels.

11. A method of packaging a medical instrument in a medical container, the medical instrument including a distal end, the medical container comprising a base having an edge at a perimeter, a first channel leading to an enlarged cavity, and a second channel leading to an enlarged cavity, wherein the second channel is nonaligned with the first channel, the medical container further comprising a cover and a locking portion, wherein the first channel and second channel fork from a common channel and the common channel extends away from the first and second channels to the edge, the method comprising:

placing a portion of the medical instrument in the common channel;

placing the distal end of the medical instrument in an enlarged cavity corresponding to one of the first and second channels depending on a shape of the medical instrument; and closing the cover onto the base, wherein closing the cover causes the locking portion to secure the cover in the closed position, secures the medical instrument in the common channel and the enlarged cavity corresponding to one of the first and second channels, and leaves the common channel laterally open at the edge.

12. The method according to claim 11, wherein the medical instrument includes a handle and the medical container includes an instrument post, the method further comprising:

securing the handle of said medical instrument to the instrument post.

13. The method according to claim 12, wherein securing the handle of said medical instrument to the instrument post includes pressing the handle onto the instrument post.

14. A method of packaging using a medical container comprising a base having an edge at a perimeter, a first channel having a first curvature along the first channel and leading to a cavity configured to receive an end of a medical instrument of a first shape, and a second channel having a second curvature along the second channel and leading to a cavity configured to receive an end of a medical instrument of a second shape, a cover, and a locking portion, wherein the first channel extends from the cavity corresponding to the second channel, and the second channel extends to the edge the method comprising:

placing a portion of the medical instrument of the first shape and the medical instrument of the second shape in at least one of the first and second channels;

placing the end of the medical instrument of the first shape and the medical instrument of the second shape in the corresponding cavity depending on the shape of the medical instrument; and closing the cover onto the base, wherein closing the cover causes the locking portion to secure the cover in the closed position, secures the end of the one of the medical instrument of the first shape and the medical instrument of the second shape in the corresponding cavity, and leaves the second channel laterally open at the edge.

15. The method according to claim 14, wherein the one of the medical instrument of the first shape and the medical instrument of the second shape includes a hand and the medical container includes an instrument post, the method further comprising:

securing the handle of the one of the medical instrument of the first shape and the medical instrument of the second shape to the instrument post.

16. The method according to claim 15, wherein securing the handle of the one of the medical instrument of the first shape and the medical instrument of the second shape to the instrument post includes pressing the handle onto the instrument post.

17. The method according to claim 14, wherein the cover includes a recessed portion configured to secure the end of one of the medical instrument of the first shape and the medical instrument of the second shape in the corresponding cavity of one of the first and second channels when the cover is in the closed position, and wherein closing the cover includes securing the end of the one of the medical instrument of the first shape and the medical instrument of the second shape between the recessed portion and the corresponding cavity.

* * * * *

UNITED STATES PATENT AND TRADEMARK OFFICE
CERTIFICATE OF CORRECTION

PATENT NO.     : 6,533,116 B1
DATED          : March 18, 2003
INVENTOR(S)    : Kimberly M. Riley It is certified that error appears in the above-identified patent and that said Letters Patent is hereby corrected as shown below:

<u>Column 8,</u>
Line 4, after "channel, the first", insert -- channel --.
Line 5, after "fork", insert -- from --.

<u>Column 9,</u>
Line 22, "edge" should read -- edge, --.
Line 23, "portion of the" should read -- portion of one of the --.
Line 26, "the medical" should read -- the one of the medical --.

Signed and Sealed this

Sixth Day of May, 2003

JAMES E. ROGAN
*Director of the United States Patent and Trademark Office*